United States Patent [19]

Sasse et al.

[11] 4,239,760
[45] Dec. 16, 1980

[54] COMBATING FUNGI AND BACTERIA WITH 3-AZOLYL-BENZO-1,2,4-TRIAZINES AND 1-OXIDES THEREOF

[75] Inventors: Klaus Sasse, Berg.-Gladbach; Walter Gauss, Cologne; Paul-Ernst Frohberger, Leverkusen; Peter Kraus, Cologne; Volker Paul, Solingen, all of Fed. Rep. of Germany

[73] Assignee: Bayer Aktiengesellschaft, Leverkusen, Fed. Rep. of Germany

[21] Appl. No.: 2,053

[22] Filed: Jan. 8, 1979

[30] Foreign Application Priority Data

Jan. 20, 1978 [DE] Fed. Rep. of Germany ....... 2802488

[51] Int. Cl.$^3$ ................. C07D 253/08; A61K 31/415; A61K 31/53; C07D 403/04
[52] U.S. Cl. .................................... 424/249; 544/183
[58] Field of Search ................... 544/183; 424/249

[56] References Cited

U.S. PATENT DOCUMENTS

| | | | |
|---|---|---|---|
| 2,489,355 | 11/1949 | Wolf et al. | 544/183 |
| 2,489,359 | 11/1949 | Wolf et al. | 544/183 |
| 3,318,947 | 5/1967 | Speciale et al. | 260/482 |
| 3,562,270 | 2/1971 | Wagner-Jauregg et al. | 544/183 |
| 4,091,098 | 5/1978 | Lumma | 544/183 |

FOREIGN PATENT DOCUMENTS

| | | |
|---|---|---|
| 83869 | 8/1971 | German Democratic Rep. |
| 2306512 | 8/1974 | Fed. Rep. of Germany ........... 544/183 |
| 2404375 | 8/1974 | Fed. Rep. of Germany ........... 544/183 |

Primary Examiner—John M. Ford
Attorney, Agent, or Firm—Sprung, Felfe, Horn, Lynch & Kramer

[57] ABSTRACT

3-Azolyl-benzo-1,2,4-triazines or 1-oxides thereof of the formula

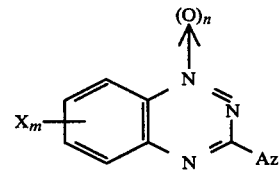

in which
X represents halogen, $C_1$–$C_4$ alkyl, $C_1$–$C_4$ alkoxy, $C_1$–$C_4$ alkylmercapto, $C_1$–$C_4$ alkylsulphonyl, nitro or trifluoromethyl,
m represents 0, 1, 2, 3 or 4, the substituents X being selected independently of one another when m is 2 or more,
n represents 0 or 1 and
Az represents a five-membered hetero-aromatic ring with 2 or 3 nitrogen atoms, which is bonded via nitrogen and which can be optionally substituted, which possess fungicidal and bactericidal properties.

9 Claims, No Drawings

COMBATING FUNGI AND BACTERIA WITH 3-AZOLYL-BENZO-1,2,4-TRIAZINES AND 1-OXIDES THEREOF

The present invention relates to and has for its objects the provision of particular 3-azolyl-benzo-1,2,4-triazines and 1-oxides thereof which possess pesticidal properties, active compositions in the form of mixtures of such compounds with solid and liquid dispersible carrier vehicles, and methods for producing such compounds and for using such compounds in a new way especially for combating pests, e.g. fungi and bacteria, with other and further objects becoming apparent from a study of the within specification and accompanying examples.

It has already been disclosed that benzo-1,2,4-triazine 1-oxides with halogen, amino, hydrazino, alkoxy and alkylmercapto substituents in the 3-position have fungicidal, herbicidal and acaricidal properties (see German Democratic Republic Patent Specification No. 83,869). However, fungicidal properties were discovered (in vitro) only in compounds with chlorine substituents in the 3-position. These substances have not acquired importance in practice. Furthermore, it is known from U.S. Pat. No. 4,067,981 that 3-alkoxy-benzo-1,2,4-triazines with additional substituents in the 7-position have a fungicidal and bactericidal action. However, their spectrum of action is relatively limited. Their action focuses on Helminthosporium species and rust diseases. The bactericidal action against Xanthomonas species is insufficient for them to be used in practice.

The present invention now provides, as new compounds, the 3-azolyl-benzo-1,2,4-triazines and -benzo-1,2,4-triazine 1-oxides of the general formula

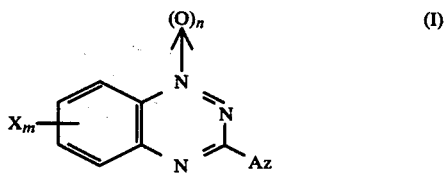

in which
X represents halogen, $C_1$–$C_4$ alkyl, $C_1$–$C_4$ alkoxy, $C_1$–$C_4$ alkylmercapto, $C_1$–$C_4$ alkylsulphonyl, nitro or trifluoromethyl,
m represents 0, 1, 2, 3 or 4, the X substituents being selected independently of one another when m is 2 or more,
n represents 0 or 1 and
Az represents a five-membered hetero-aromatic ring with 2 or 3 nitrogen atoms, which is bonded via nitrogen and which can be optionally substituted.
Preferably, X represents chlorine, bromine, methyl, trifluoromethyl, methoxy, methylmercapto or nitro; m represents 0, 1, 2 or 3; and
Az represents a group of the formula

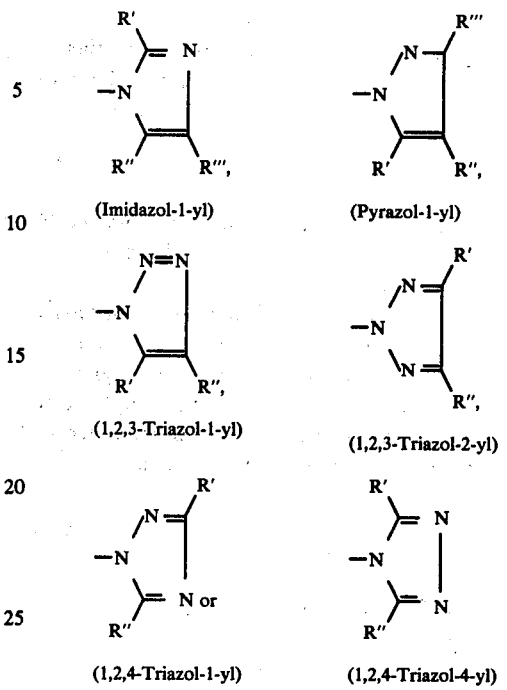

in which R', R", R''', which are selected independently of one another, each represent hydrogen, alkyl, alkoxy or alkylmercapto with 1 to 6 carbon atoms in each case, halogen, hydroxyl, aryl, aryl-$C_{1-4}$-alkyl, amino, a monoalkylamino or dialkylamino group with 1 to 2 carbon atoms in each alkyl group, $C_{1-4}$-alkoxy-$C_{1-4}$-alkoxy, $C_{1-4}$-alkanoylamino, carboxyl, $C_{1-4}$-alkoxy-carbonyl, carboxamido, N-($C_{1-4}$-alkyl)-carboxamido, or cyano.

The compounds of the general formula I in which n is 1 (one) are preferred in view of their better availability.

Compared with the above-mentioned substances of the prior art, which are related only in a relatively wide sense, the compounds according to the invention have a significantly broader spectrum of fungicidal and bactericidal action against plant pathogens. Their outstanding bactericidal properties, for example against Xanthomonas species, for the combating of which completely satisfactory agents have not hitherto been available, are to be particularly singled out. The active compounds according to the invention thus represent a valuable enrichment of the art.

The invention also provides a process for the preparation of a 3-azolyl-benzo-1,2,4-triazine or -benzo-1,2,4-triazine 1-oxide of the formula (I) in which (a) a benzo-1,2,4-triazine(1-oxide), substituted in the 3-position, of the general formula

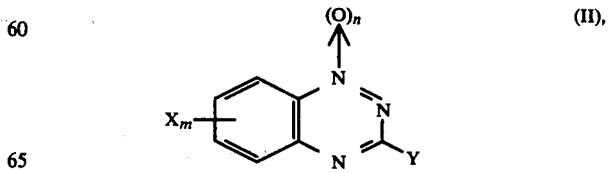

in which
X, m and n have the above-mentioned meanings and

Y represents halogen (especially chlorine or bromine) or a hydroxyl or sulpho group,
is reacted with an optionally substituted five-membered hetero-aromatic ring compound (an azole) of the general formula H—Az     (III), in which Az has the meaning stated above and the H atom shown is bonded to a N atom of the five-membered heterocyclic ring system,
and the reaction product thereby obtained is optionally subjected to subsequent reduction in the 1-position, or (b), in the case of the preparation of a pyrazolyl compound (Az in formula (I) then represents an optionally substituted pyrazolyl radical), a 3-hydrazino-benzo-1,2,4-triazine(1-oxide) of the general formula

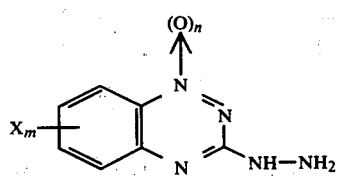

in which X, m and n have the meanings stated above, is reacted with a 1,3-dicarbonyl compound or β-oxocarboxylic acid derivative, or a compound which is capable of liberating a 1,3-dicarbonyl compound or a β-oxocarboxylic acid during the course of the reaction, and the reaction product is optionally subjected to subsequent reduction in the 1-position.

If, according to process variant (a), 3-chlorobenzo-1,2,4-triazine 1-oxide and imidazole, or benzo-1,2,4-triazine-(1-oxide)-3-sulphonic acid and 1,2,4-triazole, are used as starting materials, the course of the reaction can be represented by the equations which follow:

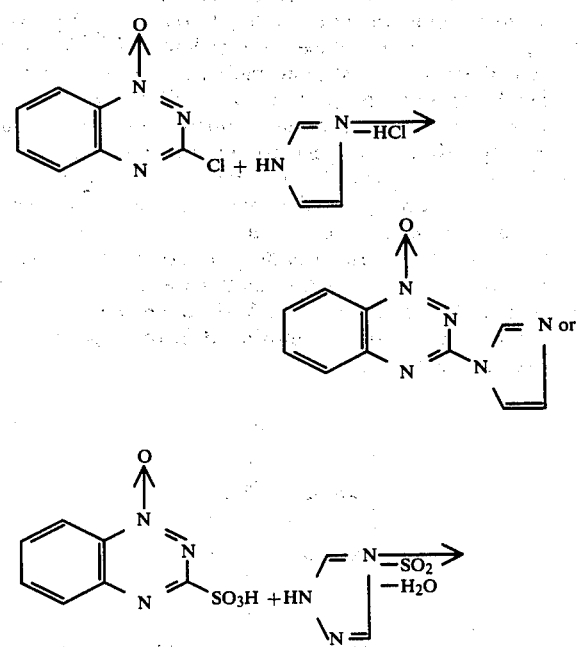

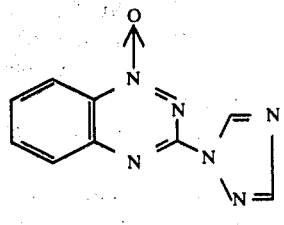

If, according to process variant (b), 7-chloro-3-hydrazino-benzotriazine 1-oxide and acetylacetone or 1,1,3,3-tetramethoxy-propane are used as the reactants, the reaction takes the following course:

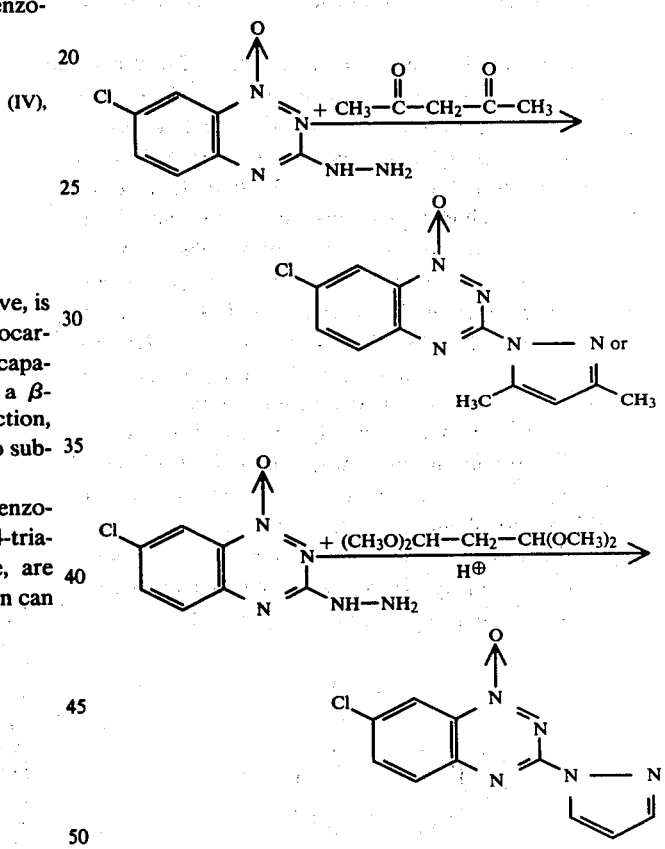

If a reduction of the N-oxides is additionally carried out after process (a) or (b), such a reaction can be represented as follows, the reaction of 7-chloro-3-pyrazolyl-benzo-1,2,4-triazine 1-oxide with catalytically activated hydrogen being outlined as an example:

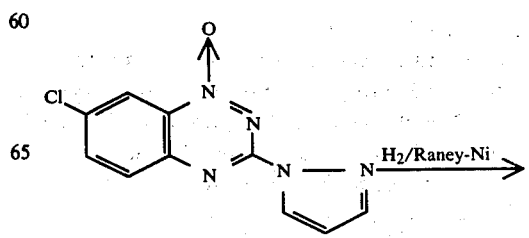

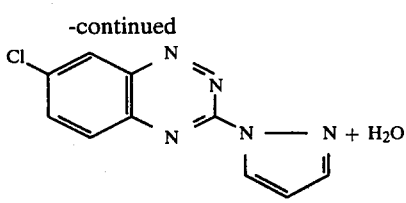 + H₂O

However, the oxygen-free (in the 1-position) 3-pyrazol-1-yl-benzotriazines can also be obtained by process variant (b) by reacting 3-hydrazino-benzotriazines (n in formula (IV) represents the number 0), instead of 3-hydrazino-benzotriazine 1-oxides, with 1,3-dicarbonyl compounds or derivatives thereof. Using 3-hydrazino-benzotriazine and acetylacetone as the reactants, the reaction takes the following course:

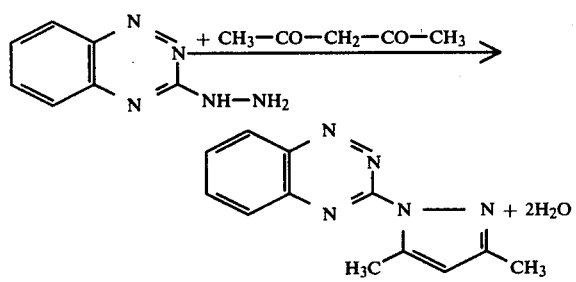

Compounds of the formula (II) are known and are obtained, for example, by the action of phosphorus oxyhalides on 3-hydroxy-benzotriazine-1-oxides (see, for example, J. Chem. Soc. 1957, 3186; J. Org. Chem. 24, 813 (1959)). 3-Chloro-benzotriazine 1-oxides correspondingly substituted in the benzene nucleus can be prepared in a completely analogous way. Benzotriazine-(1-oxide)-3-sulphonic acids can be prepared by oxidation of 3-mercapto-benzotriazine 1-oxides according to the statements in the literature.

Examples which may be mentioned of compounds of the formula (III) are: pyrazole, 3-methyl-pyrazole, 4-methyl-pyrazole, 3-ethyl-pyrazole, 4-ethyl-pyrazole, 4-propyl-pyrazole, 4-isopropyl-pyrazole, 4-butyl-pyrazole, 4-pentyl-pyrazole, 4-phenyl-pyrazole, 4-benzyl-pyrazole, 3,4-dimethyl-pyrazole, 3,5-dimethyl-pyrazole, 3,4-diethyl-pyrazole, 3,5-diethyl-pyrazole, 4-chloro-pyrazole, 4-bromo-pyrazole, 3,5-dimethyl-4-chloro-pyrazole, 3,5-dimethyl-4-bromo-pyrazole, 4-methoxy-pyrazole, 4-ethoxy-pyrazole, 4-propoxy-pyrazole, 4-isopropoxy-pyrazole, 4-methoxyethoxy-pyrazole, imidazole, 2-methyl-imidazole, 2-butyl-imidazole, 2,4,5-trimethyl-imidazole, 2-methoxy-imidazole, 2-methyl-mercapto-imidazole, 4,5-dichloro-imidazole, 2-acetamino-imidazole, 4,5-dichloro-imidazole-2-carboxylic acid methyl ester, 4,5-dichloro-imidazole-2-carboxylic acid dimethylamide, 4,5-dichloro-2-cyano-imidazole, 1,2,3-triazole, 4,5-dimethyl-1,2,3-triazole, 4-phenyl-1,2,3-triazole, 4,5-diphenyl-1,2,3-triazole, 1,2,3-triazole-4-carboxylic acid ethyl ester, 1,2,3-triazole-4,5-dicarboxylic acid diethyl ester, 1,2,4-triazole, 3-methyl-1,2,4-triazole, 3-methylmercapto-1,2,4-triazole and 3-amino-1,2,4-triazole.

3-Hydrazino-benzo-triazine 1-oxides represented by the formula (IV) are known (see, for example J. Chem. Soc. 1957, 3186 and J. Org. Chem. 24, 813 (1959)) and can be prepared by known processes, for example by reacting 3-chloro-benzotriazine 1-oxides with hydrazine. 3-Hydrazino-benzo-1,2,4-triazine, which is not oxidized in the 1-position, is also known (see the two publications mentioned above). The 3-hydrazino-benzotriazines with substituents in the benzene nucleus can be prepared completely analogously, by subjecting 3-hydrazino-benzotriazine 1-oxides to reduction. The reduction conditions are generally the same as those described for the corresponding reduction of 3-azolyl-benzo-1,2,4-triazine 1-oxides (formula (I) wherein n represents 1). Hydrogen sulphides are examples of particularly suitable reducing agents.

1,3-Dicarbonyl compounds and β-oxocarboxylic acid derivatives which are also required as reactants for process variant (b) are known. Examples are: malondialdehyde (propane-1,3-dione), chloromalondialdehyde, bromomalondialdehyde, 2-methyl-propane-1,3-dione, butane-1,3-dione, pentane-1,3-dione, pentane-2,4-dione (acetylacetone), heptane-3,5-dione, 3-dimethylamino-acrolein, 2-methyl-3-dimethylamino-acrolein, 2-ethyl-3-dimethylamino-acrolein, 2-propyl-3-dimethylamino-acrolein, 2-methoxy-3-dimethylamino-acrolein, 2-ethoxy-3-dimethylamino-acrolein, 2-propoxy-3-dimethylamino-acrolein, 2-isopropoxy-3-dimethylamino-acrolein, 1,1,3,3-tetramethoxy-propane, 4,4-dimethoxy-butan-2-one (acetoacetaldehyde dimethyl acetal), formylacetic acid ethyl ester, acetoacetic acid methyl ester, acetoacetic acid ethyl ester, diketene, cyanoacetone, cyanoacetophenone, α-cyanophenylacetaldehyde, ethoxymethylenecyanoacetic acid ethyl ester and ethoxymethylenemalononitrile.

If the procedure is according to process variant (a), the reaction is carried out in a suitable diluent. Possible diluents are inert solvents, such as, for example, aliphatic or aromatic hydrocarbons, halogenated hydrocarbons, ethers (such as diethyl ether, tetrahydrofuran, dioxane and glycol dimethyl ether), esters (for example ethyl acetate), ketones (for example acetone and methyl isobutyl ketone), dimethylformamide, dimethylsulphoxide or mixtures thereof with water.

In carrying out process variant (a), acid-binding agents are also required as auxiliaries if those compounds of the formula (II) in which Y represents halogen or the SO₃H group are used. It is appropriate to add at least the equimolar amount of a base in order to bond the acid liberated during the reaction. Bases which can be used are alkaline earth metal oxides and hydroxides, alkali metal carbonates and acetates, alkaline earth metal carbonates and acetates, tertiary amines or heterocyclic nitrogen bases, or also a second mol of the azole employed as a reactant. However, the procedure can also be to use the tertiary amine employed as the acid-binding agent (for example pyridine) in excess, and thus simultaneously as the solvent. Furthermore, it is also possible to employ metal derivatives of the azoles, for example their alkali metal compounds, halogeno-magnesium derivatives or also their N-trialkylsilyl derivatives, a separate acid-binding agent being spared.

In the case where those compounds of the formula (II) in which Y denotes an OH group are employed, a water-binding substance is necessary, as a condensing agent. Phosphorus oxychloride has proved particularly useful for this and must be used in at least the equimolar amount, it being possible for inert solvents, for example aliphatic and aromatic (chloro-)hydrocarbons, to serve as diluents. However, it is appropriate to use phosphorus oxychloride in excess, and in particular in an amount such that the reaction mixture remains stirrable in the liquid form.

The reaction temperatures in process variant (a) can be varied within a substantial range. In general, the reaction is carried out at from 0° to 130° C., preferably at from 15° to 100° C.

In the case of the reaction according to process variant (a) of benzo-1,2,4-triazine 1-oxides of the formula (II) (wherein n represents the number 1) with azoles of the formula (III), reaction products of the formula (I) that contain the N-oxide grouping in the 1-position are obtained. Subsequent reduction is necessary if it is desired to convert these products into compounds of the formula (I) which are not oxidized in the 1-position. Various reducing agents are suitable for this reduction, for example nascent hydrogen (obtained from zinc, tin or iron and an acid) or catalytically activated hydrogen using, for example, Raney nickel as the catalyst, or sulphur-containing acids of low valency levels or salts thereof, for example sulphides, dithionites, sulphites and the like. These reduction reactions are preferably carried out in an alcohol, tetrahydrofuran, dioxane or dimethylformamide, optionally mixed with water. The reaction temperatures are generally 0° to 100° C., preferably 10° to 70° C.

A reduction reaction of this nature may also be appropriate after variant (b), as indicated above.

In carrying out process variant (a) according to the invention, the compound of the formula (II) and the azole of the formula (III) are preferably employed in equimolar amounts. However, amounts of up to about 20% less than or more than the equimolar amounts are acceptable, without a substantial change in the yield. Working up can appropriately be carried out by distilling off the bulk of the mixture, diluting the residue with water, adding very dilute hydrochloric acid if bases are present and filtering off and drying the product obtained. For purification, the crude product can be recrystallized from a suitable solvent.

As already mentioned, process variant (b) can also be used for the preparation of those compounds of the formula (I) according to the invention in which Az denotes the radical of a pyrazole. In this process, a 3-hydrazino-benzo-1,2,4-triazine or -1,2,4-triazine 1-oxide of the formula (IV) is reacted with a 1,3-dicarbonyl compound or a β-oxocarboxylic acid derivative; instead of the latter compound, it is also possible to use a substance which is capable of liberating a 1,3-dicarbonyl compound or β-oxocarboxylic acid.

The reaction according to process variant (b) can be carried out in all the customary diluents which do not themselves undergo a reaction with hydrazine compounds or carbonyl compounds. Examples of such suitable diluents are: aliphatic and aromatic (halogeno-)hydrocarbons, ethers (such as diethyl ether, tetrahydrofuran or dioxane), alcohols, dimethylformamide, dimethylsulphoxide and the like, and also water or mixtures of any of the above-mentioned solvents with water.

Auxiliaries are frequently necessary in process variant (b): if, specifically, acetals or ketals of the 1,3-dicarbonyl compounds are employed, it is as a rule necessary to add a carboxylic acid or mineral acid, for example hydrochloric acid, sulphuric acid or acetic acid, in order to free the carbonyl groups in these compounds. Catalytic amounts of, for example 1 mol % of these mineral acids are often adequate for this purpose, but in individual cases it can also be appropriate to use them in equimolar amounts.

The reaction temperatures in process variant (b) can be varied within a substantial range. In general, the reaction is carried out at from 0° to 100° C., preferably from 10° to 80° C.

In carrying out process variant (b), the hydrazino compound of the formula (IV) and the 1,3-dicarbonyl compound are preferably employed in an equimolar ratio, but it is also possible, and does not impair the separation of the reaction products, for the 1,3-dicarbonyl compound to be used in excess (for example up to one additional mol). Working up of the reaction mixture is simple in that the reaction product precipitates, usually after cooling, and can be filtered off without further operations.

Compounds of the formula (I) according to the invention which may be mentioned as examples are: 3-pyrazol-1-yl-benzotriazine 1-oxide, 3-pyrazol-1-yl-benzotriazine, 3-imidazol-1-yl-benzotriazine 1-oxide, 3-imidazol-1-yl-benzotriazine, 3-triazol-1-yl-benzotriazine 1-oxide, 3-triazol-1-yl-benzotriazine, 3-pyrazol-1-yl-6-chlorobenzotriazine, 3-imidazol-1-yl-6-chloro-benzotriazine, 3-imidazol-1-yl-6-chloro-benzotriazine 1-oxide, 3-pyrazol-1-yl-7-chloro-benzotriazine 1-oxide, 3-pyrazol-1-yl-7-chloro-benzotriazine, 3-(3-methyl-pyrazol-1-yl)-7-chloro-benzotriazine, 3-(3,5-dimethyl-pyrazol-1-yl)-7-chloro-benzotriazine, 3-(3,4,5-trimethyl-pyrazol-1-yl)-7-chloro-benzotriazine 1-oxide, 3-(4-ethyl-pyrazol-1-yl)-7-chloro-benzotriazine 1-oxide, 3-(4-chloro-pyrazol-1-yl)-7-chloro-benzotriazine 1-oxide, 3-(4-methoxy-pyrazol-1-yl)-7-chloro-benzotriazine 1-oxide, 3-(4-isopropoxy-pyrazol-1-yl)-7-chloro-benzotriazine 1-oxide, 3-(5-amino-4-carbethoxypyrazol-1-yl)-7-chloro-benzotriazine 1-oxide, 3-(5-hydroxy-pyrazol-1-yl)-7-chloro-benzotriazine, 3-(3-methyl-5-hydroxy-pyrazol-1-yl)-7-chloro-benzotriazine 1-oxide, 3-(3-methyl-5-hydroxy-pyrazol-1-yl)-7-chloro-benzotriazine, 3-imidazol-1-yl-7-chloro-benzotriazine 1-oxide, 3-imidazol-1-yl-7-chloro-benzotriazine, 3-(2-methyl-imidazol-1-yl)-7-chloro-benzotriazine, 3-(2,4,5-trimethyl-imidazol-1-yl)-7-chloro-benzotriazine, 3-(2-methoxy-imidazol-1-yl)-7-chloro-benzotriazine, 3-(2-methylmercapto-imidazol-1-yl)-7-chloro-benzotriazine, 3-(4,5-dichloro-imidazol-1-yl)-7-chloro-benzotriazine, 3-(2-acetamido-imidazol-1-yl)-7-chloro-benzotriazine, 3-(4,5-dichloro-2-cyano-imidazol-1-yl)-7-chloro-benzotriazine, 3-(1,2,3-triazol-1-yl)-7-chloro-benzotriazine 1-oxide, 3-(1,2,3-triazol-1-yl)-7-chloro-benzotriazine, 3-(1,2,3-triazol-2-yl)-7-chloro-benzotriazine 1-oxide, 3-(1,2,3-triazol-2-yl)-7-chloro-benzotriazine, 3-(1,2,4-triazol-1-yl)-7-chloro-benzotriazine 1-oxide, 3-(1,2,4-triazol-1-yl)-7-chloro-benzotriazine, 3-(3-methyl-1,2,4-triazol-1-yl)-7-chloro-benzotriazine, 3-(3-methylmercapto-1,2,4-triazol-1-yl)-7-chloro-benzotriazine, 3-(3-amino-1,2,4-triazol-1-yl)-7-chloro-benzotriazine, 3-pyrazol-1-yl-5,7-dichloro-benzotriazine, 3-(3,5-dimethyl-pyrazol-1-yl)-5,7-dichloro-benzotriazine 1-oxide, 3-(4-ethyl-pyrazol-1-yl)-5,7-dichloro-benzotriazine, 3-(4-chloro-pyrazol-1-yl)-5,7-dichloro-benzotriazine, 3-(4-methoxy-pyrazol-1-yl)-5,7-dichloro-benzotriazine, 3-imidazol-1-yl-5,7-dichloro-benzotriazine 1-oxide, 3-imidazol-1-yl-5,7-dichloro-benzotriazine, 3-triazol-1-yl-5,7-dichloro-benzotriazine 1-oxide, 3-triazol-1-yl-5,7-dichloro-benzotriazine, 3-pyrazol-1-yl-6,7-dichloro-benzotriazine, 3-imidazol-1-yl-6,7-dichlorobenzotriazine, 3-pyrazol-1-yl-5,7,8-trichloro-benzotriazine, 3-imidazol-1-yl-5,7,8-trichloro-benzotriazine, 3-pyrazol-1-yl-7-bromo-benzotriazine, 3-imidazol-1-yl-7-bromo-benzotriazine, 3-pyrazol-1-yl-7-methyl-benzotriazine, 3-imidazol-1-yl-7-methyl-benzotriazine, 3-pyrazol-1-yl-7-butylbenzotriazine, 3-pyrazol-1-yl-7-trifluoromethylbenzotriazine, 3-imidazol-1-yl-7-trifluoromethyl-benzotriazine 1-oxide, 3-imidazol-1-yl-7-trifluoromethyl-benzotriazine, 3-pyrazol-1-yl-7-methoxy-benzotriazine, 3-pyrazol-1-yl-7-butoxy-benzotriazine, 3-imidazol-1-yl-7-methylmercaptobenzotriazine, 3-imidazol-1-yl-7-butyl-mercapto-benzotriazine, 3-imidazol-1-yl-7-methylsulphonyl-benzotriazine, 3-imidazol-1-yl-7-nitro-benzotriazine 1-oxide and 3-triazol-1-yl-7-nitro-benzotriazine 1-oxide.

The active compounds according to the invention exhibit a powerful fungitoxic action and bactericidal action. They do not damage crop plants in the concentrations required for combating fungi and bacteria. For these reasons, they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

Bactericidal agents are employed in plant protection for combating bacteria of the Pseudomonadaceae family, for example *Pseudomonas solanacearum, Pseudomonas lachrymans, Pseudomonas syringae, Xanthomonas citri, Xanthomonas oryzae* and *Xanthomonas vesicatoria,* of the Enterobacteriaceae family, for example *Erwinia amylovora,* and of the Corynebacteriaceae family, and furthermore of the Rhizobiaceae family, for example *Agrobacterium tumefaciens.*

The active compounds display a high degree of action and a broad spectrum of action. They are simple to handle and can be employed in practice for combating undesired fungal and bacterial growth.

Since they are well tolerated by plants, they can be used against fungal and bacterial plant diseases by treating the standing cultivated plants or individual parts thereof, or the seed or also the arable land. The active compounds are particularly effective against bunt of wheat (*Tilletia caries*), stripe disease of barley (*Helminthosporium gramineum* syn. *Drechslera graminea*) and powdery mildew of apples (*Podosphaera leucotricha*), and have a high activity against Xanthomonas species.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides and leaf bactericides, the active compound concentrations in the use forms can be varied within a substantial range. They are, in general, from 0.5 to 0.0005% by weight, preferably from 0.2 to 0.001%.

For the treatment of seed, amounts of active compound of 0.001 to 50 g, preferably 0.01 to 5 g, are generally employed per kilogram of seed.

For the treatment of soil, amounts of active compound of 1 to 1,000 g, preferably 10 to 200 g, are generally employed per cubic meter of soil.

The present invention also provides a fungicidal or bactericidal composition containing as active ingredient a compound of the present invention in admixture with a solid or liquefied gaseous diluent or carrier or in admixture with a liquid diluent or carrier containing a surface-active agent.

The present invention also provides a method of combating fungi or bacteria which comprises applying to the fungi or bacteria, or to a habitat thereof, a compound of the present invention alone or in the form of a composition containing as active ingredient a compound of the present invention in admixture with a diluent or carrier.

The present invention further provides crops protected from damage by fungi or bacteria by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

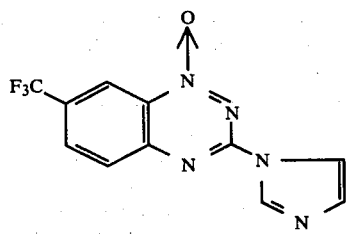

(1)

Process variant (a)

A mixture of 7 g (0.103 mol) of imidazole, 10.1 g (0.1 mol) of triethylamine and 50 ml of dioxan was added dropwise to a solution of 25 g (0.1 mol) of 3-chloro-7-trifluoromethylbenzo-1,2,4-triazine 1-oxide in 100 ml of dioxane at room temperature. The reaction mixture was heated gradually to the boil and boiled under reflux for 5 hours. After cooling, three times the volume of water was added and the reaction product was filtered off and dried. 17 g of 3-imidazol-1-yl-7-trifluoromethyl-benzo-1,2,4-triazine 1-oxide of melting point 128° C. (recrystallized from wash benzine) were obtained, that is to say 60.5% of theory.

EXAMPLE 2

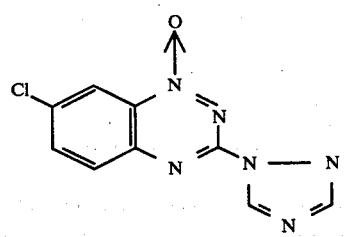

(2)

Process variant (a)

21.6 g (0.1 mol) of 3,7-dichloro-benzo-1,2,4-triazine 1-oxide were introduced, in portions, into a solution of 6.9 g (0.1 mol) of triazole in 50 ml of pyridine at room temperature, while stirring. The mixture was stirred at room temperature for 1 hour and then boiled under reflux for 3 hours. The pyridine was distilled off in vacuo, the residue was stirred with very dilute hydrochloric acid and the product was filtered off, washed with dilute hydrochloric acid and water and dried. 18 g of 3-(1,2,4-triazol-1-yl)-7-chloro-benzo-1,2,4-triazine 1-oxide of melting point 204°-205° C. (recrystallized from butanol) were obtained, that is to say 72.6% of theory.

EXAMPLE 3

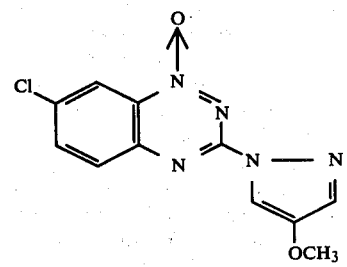

(3)

Process variant (a)

3.45 g (0.115 mol) of sodium hydride (80% pure) were introduced into a solution of 12.6 g (0.13 mol) of 4-methoxy-pyrazole in 100 ml of absolute dimethylformamide at room temperature and the mixture was subsequently warmed briefly to 60° C. 21.6 g (0.1 mol) of 3,7-dichloro-benzo-1,2,4-triazine 1-oxide were added in portions to the mixture, which had been cooled to room temperature. After the exothermic reaction had subsided, the mixture was subsequently stirred at 30° to 40° C. for a further 3 hours and the reaction product was then precipitated with water. This product was filtered off, stirred in 150 ml of methanol, filtered off again and dried. 17.3 g of 3-(4-methoxypyrazol-1-yl)-7-chloro-benzo-1,2,4-triazine 1-oxide of melting point 253°-255° C. (with decomposition) were obtained, that is to say 62.3% of theory. The compound could be recrystallized from dimethylformamide.

The following compounds of the general formula

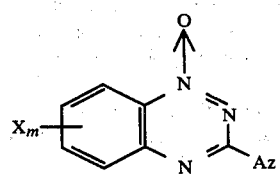

(IA)

were obtained in a corresponding manner:

TABLE 1

| Compound No. | $X_m$ | Az | Melting point (°C.) |
|---|---|---|---|
| 4 | 7-Cl | (pyrazolyl with Cl) | 268–270 (decomposition) |
| 5 | 7-Cl | (pyrazolyl) | 172 |
| 6 | 6-Cl, 7-Cl | (pyrazolyl) | 200 |
| 7 | 5-Cl, 7-Cl | (pyrazolyl with Cl) | 210–211 |
| 8 | 5-Cl, 7-Cl | (pyrazolyl with OCH₃) | 224–226 |
| 9 | 5-Cl, 7-Cl | (pyrazolyl) | 144 |
| 10 | 5-Cl, 7-Cl | (triazolyl) | 206 |
| 11 | 7-Br | (pyrazolyl) | 160 |

EXAMPLE 4

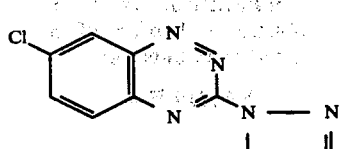

(12)

Reduction 24.8 g (0.1 mol) of 3-pyrazol-1-yl-7-chloro-benzo-1,2,4-triazine 1-oxide were hydrogenated in 150 ml of ethanol at 25° to 30° C. in the presence of Raney nickel under a hydrogen pressure of 50 bars, until the pressure remained constant. The catalyst was filtered off and the solution was evaporated in vacuo. 3-(Pyrazol-1-yl)-7-chloro-benzo-1,2,4-triazine of melting point 188° C. was obtained in virtually quantitative yield. The compound could be recrystallized from toluene.

The following compounds of the general formula

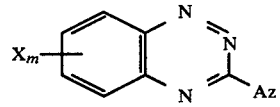

(IB)

were obtained in a corresponding manner:

TABLE 2

| Compound No. | $X_m$ | Az | Melting point (°C.) |
|---|---|---|---|
| 13 | 6-Cl | (pyrazolyl) | 110 |
| 14 | 7-Cl | (pyrazolyl with CH₃) | 168 |
| 15 | 7-Cl | (pyrazolyl with two CH₃) | 174 |
| 16 | 7-Cl | (pyrazolyl) | 158 |
| 17 | 7-Cl | (triazolyl) | 194 |
| 18 | 7-Cl | (pyrazolyl with Cl) | 228.5–229.5 |
| 19 | 7-Cl | (pyrazolyl with three CH₃) | 194–195 |
| 20 | 5-Cl, 7-Cl | (pyrazolyl) | >250 |
| 21 | 5-Cl, 7-Cl | (pyrazolyl with CH₃) | 176 |
| 22 | 5-Cl, 7-Cl | (pyrazolyl with two CH₃) | 124 |

(a) Preparation of starting materials

3-Hydrazino-benzo-1,2,4-triazine 1-oxides (Precursor A)

1 mole of a 3-chloro-benzo-1,2,4-triazine 1-oxide was introduced in portions into a mixture of 200 g (4 moles) of hydrazine hydrate and 1.2 liters of dioxane at room temperature in the course of 1 hour, while stirring. After the slightly exothermic reaction had subsided, the mixture was subsequently stirred at 50° to 60° C. for a further 3 hours. After cooling to 15° to 20° C., the reaction product which had precipitated was filtered off, washed with a little dioxane and then with water and dried. A further quantity of the reaction product could be obtained by concentrating the dioxane solution or (in a less pure form) by precipitating with water.

The following 3-hydrazino-benzo-1,2,4-triazine 1-oxides were obtained in this manner, in yields of over 85%: 6-chloro-3-hydrazino-benzotriazine 1-oxide, melting point 178°-180° C.; 7-chloro-3-hydrazino-benzotriazine 1-oxide, melting point 198°-200° C. (from dimethylformamide) 5,7-dichloro-3-hydrazino-benzotriazine 1-oxide, melting point 210° C.; 6,7-dichloro-3-hydrazino-benzotriazine 1-oxide, melting point 205° C. (from glycol monomethyl ether); 7-bromo-3-hydrazino-benzotriazine 1-oxide, melting point 217° C.; 7-trifluoromethyl-3-hydrazino-benzotriazine 1-oxide, melting point 164°-166° C.; and 7-methoxy-3-hydrazino-benzotriazine 1-oxide, melting point 170°-172° C.

EXAMPLE 5

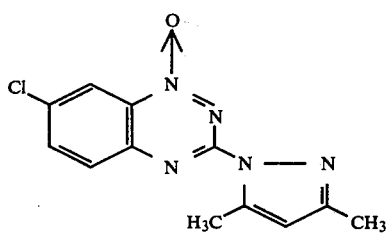
(28)

Process variant (b)

21.2 g (0.1 mol) of 7-chloro-3-hydrazino-benzo-1,2,4-triazine 1-oxide were boiled under reflux with 10 g (0.1 mol) of acetylacetone in 200 ml of ethanol for 5 hours. After cooling, the reaction product which had precipitated was filtered off, washed with ethanol and dried. 20.2 g of 3-(3,5-dimethyl-pyrazol-1-yl)-7-chlorobenzo-1,2,4-triazine 1-oxide of melting point 198°-200° C. (from dimethylformamide) were obtained, that is to say 73% of theory.

3-Hydrazino-benzo-1,2,4-triazines (Precursor B)

0.1 mole of a 3-hydrazino-benzo-1,2,4-triazine 1-oxide (precursor A) was introduced in portions into a mixture of 17.1 g (0.3 mole) of sodium bisulphide in 80 ml of water and 250 ml of dioxane at room temperature, while stirring. The mixture was subsequently stirred at room temperature for 1 hour and at 50° C. for a further 3 hours. The dioxane was then distilled off in vacuo and the residue was stirred with 200 ml of water. The reaction product, which was insoluble, was filtered off, washed with water and dried. Small amounts of sulphur which had simultaneously precipitated could be removed by washing with carbon disulphide.

The following compounds, for example, were obtained in this manner: 7-chloro-3-hydrazino-benzo-1,2,4-triazine, melting point 190°-192° C. (from dimethylformamide), in 72% yield and 5,7-dichloro-3-hydrazino-benzo-1,2,4-triazine, melting point 236°-238° C. (butanol), in 67% yield.

EXAMPLE 6

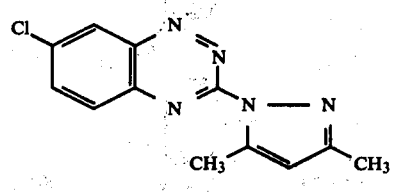
(15)

Process variant (b) [an alternative route to Compound 15]

19.5 g (0.1 mol) of 3-hydrazino-7-chloro-benzo-1,2,4-triazine and 10 g (0.1 mol) of acetylacetone were boiled under reflux in 125 ml of ethanol for 5 hours. The residue after distilling off the solvent was recrystallized from wash benzine. 22.3 g of 3-(3,5-dimethyl-pyrazol-1-yl)-7-chloro-benzo-1,2,4-triazine of melting point 174° C. were obtained, that is to say 86% of theory.

EXAMPLE 7

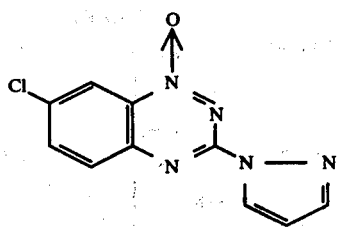
(29)

Process variant (b)

21.2 g (0.1 mole) of 7-chloro-3-hydrazino-benzo-1,2,4-triazine 1-oxide were heated under reflux with 20 g (0.12 mole of 1,1,3,3-tetramethoxypropane in 160 ml of ethanol for 5 hours, 10 ml of concentrated hydrochloric acid being added. The mixture was then cooled to room temperature and the reaction product was filtered off, washed with ethanol and dried. 18 g of 3-pyrazol-1-yl-7-chloro-benzo-1,2,4-triazine 1-oxide of melting point 210° C. (recrystallized from butanol) were obtained.

EXAMPLE 8

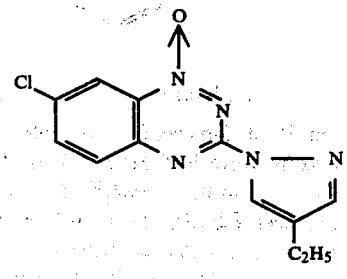
(30)

Process variant (b)

15.24 g (0.12 mole) of 2-ethyl-3-dimethylaminoacrolein were added to a mixture of 21.15 g (0.1 mole) of 3-hydrazino-7-chloro-benzo-1,2,4-triazine 1-oxide, 30 ml of methanol and 125 ml (0.25 mole) of 2 N hydrochloric acid at 60° C., whereupon the temperature rose to 68° C. The mixture was stirred at 60° C. for 8 hours and cooled to room temperature and the reaction product was filtered off. The filter cake was washed with water and methanol and dried at 110° C. 13 g of 3-(4-ethyl-pyrazol-1-yl)-7-chlorobenzo-1,2,4-triazine 1-oxide of melting point 228.5° to 230° C. (recrystallized from toluene) were obtained, that is to say 47.2% of theory.

The following compounds of the general formula

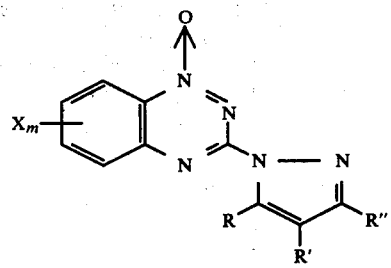

were obtained in a corresponding manner:

2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg. C.) and was then poured into Petri dishes of 9 cm diameter. Control plates to which the preparation had not been added were also set up.

When the nutrient medium had cooled and solidified, the plates were inoculated with the species of organisms stated in the table and incubated at about 21 deg. C.

The fungi species *Sclerotinia sclerotiorum, Rhizoctonia solani, Pythium ultimum, Cochliobolus miyabeanus, Pyricularia oryzae, Helminthosporium gramineum* and *Pellicularia sasakii* and the bacterium *Xanthomonas oryzae* were used in the test.

Evaluation was carried out after 4–10 days, dependent upon the speed of growth of the organisms. When evaluation was carried out the radial growth of the organism on the treated nutrient media was compared with the growth on the control nutrient medium. In the

TABLE 3

| Compound No. | Reactant | $X_m$ | R | R' | R" | Melting point (°C.) |
|---|---|---|---|---|---|---|
| 31 | 1,1,3,3-Tetramethoxy-propane | 6-Cl | H | H | H | 200 |
| 32 | 4,4-Dimethoxy-butan-2-one | 7-Cl | H | H | $CH_3$ | 112 |
| 33 | Ethoxymethylene-cyano-acetic acid ethyl ester | 7-Cl | $NH_2$ | $CO-OC_2H_5$ | H | 269–274 (with decomposition) |
| 34 | 3-Methyl-pentane-2,4-dione | 7-Cl | $CH_3$ | $CH_3$ | $CH_3$ | 228–231 |
| 35 | 2-Isopropoxy-3-dimethyl-amino-acrolein | 7-Cl | H | $OCH(CH_3)_2$ | H | 195–196 |
| 36 | 1,1,3,3-Tetramethoxypropane | 5-Cl, 7-Cl | H | H | H | 160 |
| 37 | 4,4-Dimethoxy-butan-2-one | 5-Cl, 7-Cl | H | H | $CH_3$ | 170 |
| 38 | Acetylacetone | 5-Cl, 7-Cl | $CH_3$ | H | $CH_3$ | 174 |
| 39 | 3-Methyl-pentane-2,4-dione | 5-Cl, 7-Cl | $CH_3$ | $CH_3$ | $CH_3$ | 198–202 |
| 40 | 2-Ethyl-3-dimethylamino-acrolein | 5-Cl, 7-Cl | H | $C_2H_5$ | H | |
| 41 | 1,1,3,3-Tetramethoxypropane | 7-Br | H | H | H | 220 |
| 42 | 1,1,3,3-Tetramethoxypropane | 7-$CF_3$ | H | H | H | 230 |
| 43 | 1,1,3,3-Tetramethoxypropane | 7-$OCH_3$ | H | H | H | 168 |

The fungicidal and bactericidal activity of the compounds of this invention is illustrated by the following examples wherein the compounds according to the present invention are each identified by the number (given in brackets) from the preparative examples hereinabove:

EXAMPLE 9

Agar plate test

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Composition of the solvent mixture:
0.19 part by weight of acetone or dimethylformamide
0.01 part by weight of emulsifier (alkylaryl polyglycol ether)
1.80 parts by weight of water
Ratio of solvent mixture to nutrient medium:

evaluation of the organism growth, the following characteristic values were used:
1 no growth
up to 3 very strong inhibition of growth
up to 5 medium inhibition of growth
up to 7 slight inhibition of growth
9 growth equal to that of untreated control.

In this test, for example, the following compounds showed a superior action compared to the prior art: (1), (27), (20), (9), (37), (38), (10), (16), (23), (22), (2), (24), (11), (17) and (5).

EXAMPLE 10

Bacteria test/*Xanthomonas oryzae*

Solvent: 11.75 parts by weight of acetone
Dispersing agent: 0.75 part by weight of alkylarylpolyglycol ether
Water: 987.50 parts by weight The amount of active compound required for the desired active compound concentration in the spray liquor was mixed with the stated amount of the solvent and of the dispersing agent and the concentrate was diluted with the stated amount of water.

Rice plants which were about 40 days old were sprayed with the spray liquor until dripping wet. The plants remained in a greenhouse, at temperatures of 22 to 24 deg. C. and a relative atmospheric humidity of about 70%, until they had dried. Needles were then dipped into an aqueous bacterial suspension of *Xanthomonas oryzae* and the plants were inoculated by pricking the leaves. After the inoculation, the plants stood for 24 hours at 100% relative atmospheric humidity and thereafter in a room at 26 to 28 deg. C. and 80% relative atmospheric humidity.

10 days after the inoculation, the infection of all pricked inoculated leaves of plants which had beforehand been treated with the preparation was evaluated.

In this test, for example, the following compounds showed a superior action compared to the prior art: (12), (15), (1), (43), (36) and (35).

EXAMPLE 11

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10 deg. C. in a refrigerator.

The germination of the spores on the wheat grains, each of which was contaminated with about 100,000 spores, was subsequently determined microscopically. The smaller the number of spores which had germinated, the more effective was the active compound.

In this test, for example, the following compounds showed a superior action compared to the prior art: (1), (43), (36), (25), (26), (27), (20), (9), (37), (38), (10), (23), (21), (22), (2), (24), (11), (17), (6), (31), (18) and (19).

EXAMPLE 12

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Helminthosporium gramineum*, was shaken with the dressing in a closed glass flask. The seed, on moist filter paper discs in closed Petri dishes, was exposed to a temperature of 4 deg. C. for 10 days in a refrigerator. The germination of the barley, and possibly also of the fungus spores, was thereby initiated. Two batches of 50 grains of the pregerminated barley were subsequent sown 3 cm deep in Fruhstorfer standard soil and cultivated in a greenhouse at temperatures of 18 deg. C. in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

In this test, for example, the following compounds showed a superior action compared to the prior art: (1), (26), (5), (10), (16), (23) and (2).

It will be appreciated that the instant specification and examples are set forth by way of illustration and not limitation, and that various modifications and changes may be made without departing from the spirit and scope of the present invention.

What is claimed is:

1. A method of combating phytopathogenic fungi or bacteria which comprises applying to the fungi or bacteria, or to a habitat thereof, a fungicidally or bactericidally effective amount of a compound of the formula

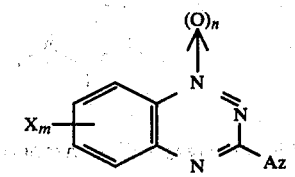

in which
X represents halogen, $C_1-C_4$ alkyl, $C_1-C_4$ alkoxy, $C_1-C_4$ alkylmercapto, $C_1-C_4$ alkylsulphonyl, nitro or trifluoromethyl, m represents 0, 1, 2, 3 or 4, the substituents X being selected independently of one another when m is 2 or more, n represents 0 or 1 and Az represents a five-membered hetero-aromatic ring with 2 or 3 nitrogen atoms, which is bonded via nitrogen and which can be optionally substituted by alkyl, alkoxy or alkylmercapto with 1 to 6 carbon atoms in each case, halogen, hydroxyl, phenyl, phenalkyl, $NH_2$, a monoalkylamino or dialkylamino group with 1 to 2 carbon atoms in the or each alkyl group, $C_{1-4}$-alkoxy-$C_{1-4}$-alkoxy, lower alkanoyl amino, carboxyl, a carboxylic acid ester or optionally N-$C_{1-4}$-alkyl-substituted carboxamido group or cyano.

2. The method according to claim 1, in which said compound is employed to combat phytopathogenic fungi.

3. A method according to claim 1, wherein such compound is 3-imidazol-1-yl-7-trifluoromethyl-benzo-1,2,4-triazine 1-oxide of the formula

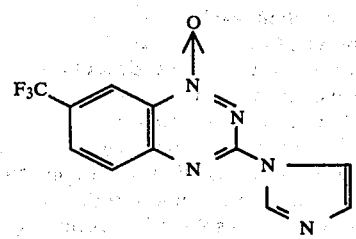

4. A method according to claim 1, wherein such compound is 3-(1,2,4-triazol-1-yl)-7-chloro-benzo-1,2,4-triazine 1-oxide of the formula

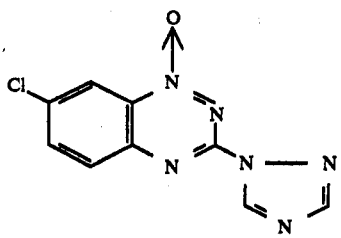

5. A method according to claim 1, where such compound is 3-(imidazol-1-yl)-7-bromo-benzo-1,2,4-triazine 1 oxide of the formula

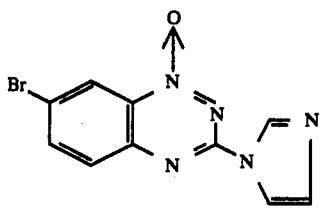

6. A method according to claim 1, wherein such compound is 3-(imidazol-1-yl)-7-chloro-benzo-1,2,4-triazine-1-oxide of the formula

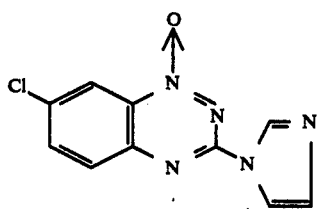

7. The method according to claim 1 in which said compound is 3-imidazol-1-yl-7-trifluoromethyl-benzo-1,2,4-triazine 1-oxide, 3-(1,2,4-triazol-1-yl)-7-chloro-benzo-1,2,4-triazine 1-oxide, 3-(imidazol-1-yl)-7-bromo-benzo-1,2,4-triazine 1-oxide, 3-(pyrazol-1-yl)-7-chloro-benzo-1,2,4-triazine, 3-(3,5-dimethyl-pyrazol-1-yl)-7-chlorobenzo-1,2,4-triazine, 3-(imidazol-1-yl)-7-chloro-benzo-1,2,4-triazine-1-oxide or 3-(imidazolyl)-7-chloro-benzo-1,2,4-triazine.

8. A compound according to claim 1, wherein
X represents chlorine, bromine, methyl, trifluoromethyl, methoxy, methylmercapto or nitro;
m represents 0, 1, 2 or 3; and
Az represents a group of the formula

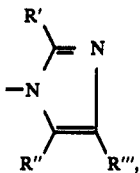 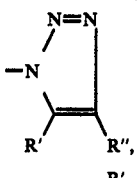

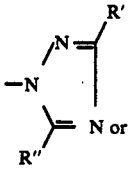 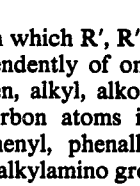

in which R', R" and R''', which are selected independently of one another, each represent hydrogen, alkyl, alkoxy, or alkylmercapto with 1 to 6 carbon atoms in each case, halogen, hydroxyl, phenyl, phenalkyl, $NH_2$, a monoalkylamino or dialkylamino group with 1 to 2 carbon atoms in the or each alkyl group, $C_{1-4}$-alkoxy-$C_{1-4}$-alkoxy, lower alkanoyl amino, carboxyl, a carboxylic acid ester or optionally N-$C_{1-4}$-alkyl-substituted carboxamido group or cyano.

9. A compound according to claim 8, wherein R', R" and R''' each independently is alkyl or alkoxy, with 1 to 5 carbon atoms, methylmercapto, clorine, bromine, phenyl, benzyl, amino, methylamino, dimethylamino, methoxycarbonyl, ethoxycarbonyl, acetylamino or cyano.

* * * * *

UNITED STATES PATENT AND TRADEMARK OFFICE
CERTIFICATE OF CORRECTION

PATENT NO. : 4239760
DATED : December 16, 1980
INVENTOR(S) : Klaus Sasse et al

It is certified that error appears in the above-identified patent and that said Letters Patent are hereby corrected as shown below:

Column 8, line 20, change "1-6" to -- 1-yl-6 --.
Column 14, add at the end thereof

| Compound No. | $X_m$ | Az | Melting point (°C) |
|---|---|---|---|
| 23 | 5-Cl, 7-Cl |  | 184 |
| 24 | 5-Cl, 7-Cl |  | 150 |
| 25 | 7-CF$_3$ |  | 210 |
| 26 | 7-CF$_3$ |  | 130 |
| 27 | 7-OCH$_3$ |  | 174 |

Signed and Sealed this

Tenth Day of March 1981

[SEAL]

Attest:

RENE D. TEGTMEYER

Attesting Officer  Acting Commissioner of Patents and Trademarks